United States Patent [19]
Jamshidi

[11] 4,163,446
[45] Aug. 7, 1979

[54] BIOPSY NEEDLE AND REMOVABLE PAD THEREFOR

[76] Inventor: Khosrow Jamshidi, 610 Winston Ct., St. Paul, Minn. 55118

[21] Appl. No.: 873,783

[22] Filed: Jan. 31, 1978

[51] Int. Cl.² ............................................. A61B 10/00
[52] U.S. Cl. .................................... 128/754; 16/121
[58] Field of Search ............... 128/2 B, 310, 347, 351; 16/118, 121; 30/301, 316, 358

[56] References Cited

U.S. PATENT DOCUMENTS

| | | | |
|---|---|---|---|
| 843,344 | 2/1907 | Linderman | 30/358 |
| 3,628,524 | 12/1971 | Jamshidi | 128/2 B |
| 3,630,192 | 12/1971 | Jamshidi | 128/2 B |
| 3,850,158 | 11/1974 | Elias et al. | 128/2 B |
| 3,893,205 | 7/1975 | Anderson et al. | 16/121 |

FOREIGN PATENT DOCUMENTS 137231  7/1960  U.S.S.R. .................................... 128/310

*Primary Examiner*—Richard T. Stouffer
*Attorney, Agent, or Firm*—Orrin M. Haugen; Thomas J. Nikolai

[57] ABSTRACT

A pad for use in combination with a bone marrow biopsy needle which is adapted to be slipped over the proximal end of the needle to provide an enlarged surface for distributing the pressure across the palm of the user. The pad includes a generally disc-shaped palm engaging surface along with a needle enveloping sleeve for releasable attachment to the biopsy needle. A bore is formed through the wall of the sleeve to provide communication between the interior of the sleeve and the atmosphere, thereby avoiding transfer of air between the pad element and the lumen of the needle when the pad element is mounted on the needle.

3 Claims, 7 Drawing Figures

BIOPSY NEEDLE AND REMOVABLE PAD THEREFOR

BACKGROUND OF THE INVENTION

The present invention relates generally to an improved biopsy needle structure, and more specifically to a palm engaging knob which may be releasably mounted on the proximal end of the needle, thereby rendering the device more comfortable in the hands of the user.

Bone marrow biopsy needles are well known, and are widely used in the collection of biopsy tissue. Bone marrow biopsy structures are illustrated and disclosed in U.S. Pat. Nos. 3,628,524, and 3,598,108. The device of the present invention is intended to be slipped over the proximal end of the needle structure following removal of the stylet, this normally occurring at the time the surgeon is commencing penetration of the bone surface.

Normally, bone marrow biopsy needles may have a proximal end which is relatively small in cross-section, and in certain instances, may be an extension of the elongated needle structure. In order to facilitate penetration of the bone, the distal end of the needle is normally sharpened, and this cutting edge, while moving relative to the surface of the bone, and with a force being applied to the bone, will accomplish penetration. In certain instances, and in some structures, the tip of the needle may be serrated or provided with rasp-like elements, depending upon the application. The force required to penetrate the bone is, of course, applied by the surgeon through the palm of his hand as the biopsy needle structure is being rotated arcuately about its axis. In order to reduce the stress concentration on the palm of the hand, the removable pad element of the present invention is provided, with the device further having a means for eliminating transfer of air into the lumen of the needle when being mounted on the needle end.

SUMMARY OF THE INVENTION

Briefly, in accordance with the present invention, the biopsy needle is provided with a pad means which is capable of removable mounting upon the hollow body member of the needle, with the pad means including a generally disc-shaped element with a palm engaging surface and a needle enveloping sleeve extending outwardly from the surface opposed to the palm engaging surface. The needle engaging sleeve has a radial extending bore formed through the wall thereof adjacent the juncture between the pad surface and the sleeve, thereby providing communication between the interior of the sleeve and atmosphere. This bore eliminates the possibility of introducing or compressing the air within the lumen of the needle structure.

Therefore, it is a primary object of the present invention to provide an attachment for a bone marrow biopsy needle which reduces the concentration of forces in the palm of the hand of the user, thereby rendering the biopsy needle more comfortable for the user.

It is a further object of the present invention to provide an improved biopsy needle structure which comprises a pad means which may be removably mounted upon the proximal end of the needle structure, and which substantially increases the area of the proximal end of the biopsy needle exposed to the palm of the hand of the user, thereby rendering the structure more comfortable during use, and further reducing the risk of tearing of the surgical glove worn by the user.

Other and further objects of the present invention will become apparent to those skilled in the art upon a study of the following specification, appended claims, and accompanying drawing.

DESCRIPTION OF THE PREFERRED EMBODIMENT

Figure 1:
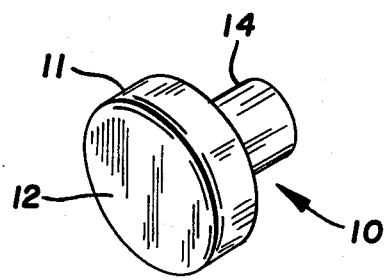
FIG. 1 is a perspective view of the pad means of the present invention, and showing the palm engaging surface thereof.
Figure 2:
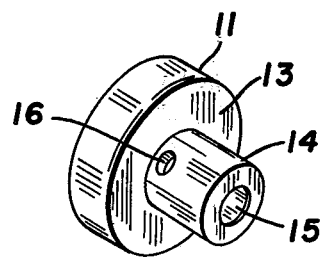
FIG. 2 is a perspective view of the pad means of the present invention, with this view showing the needle enveloping sleeve which extends outwardly from the pad.
Figure 3:
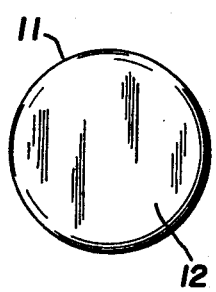
FIG. 3 is an elevational view of the palm engaging surface of the pad means.
Figure 5:
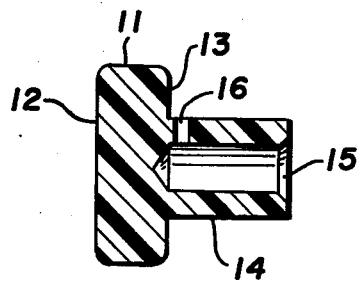
FIG. 5 is a vertical sectional view taken along the line and in the direction of the arrows 5—5 of FIG. 4, with FIG. 5 further showing the venting bore.
Figure 4:
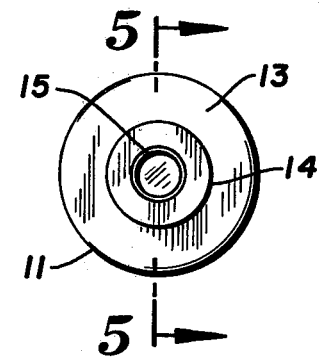
FIG. 4 is an elevational view of the pad means of the present invention, and showing the needle enveloping sleeve.

In accordance with the preferred embodiment of the present invention, the comfort pad or knob generally designated 10, and as illustrated in FIGS. 1 and 2, includes a pad element in the form of a disc 11, and with opposed major surfaces including a palm engaging surface 12 and a second surface 13 from which a needle enveloping sleeve 14 extends. The needle enveloping sleeve is provided with an internal bore as at 15, with a venting bore being provided at 16 adjacent the juncture between surface 13 and needle enveloping sleeve 14.

Figure 6:
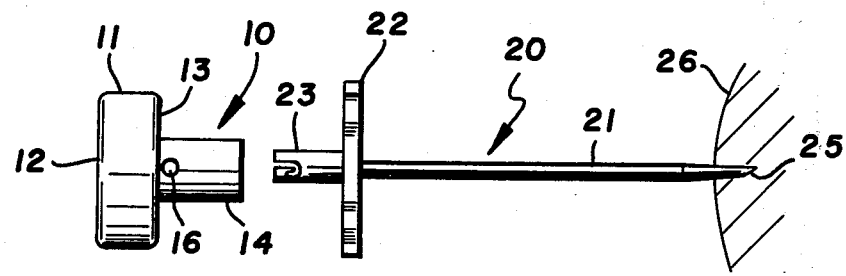
FIG. 6 is a side elevational view of a biopsy needle and pad means, with the pad means being shown separated from the biopsy needle, and with the distal end of the needle being shown in bone-engaging disposition.
Figure 7:
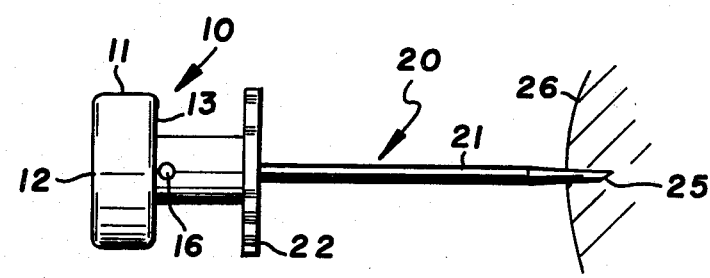
FIG. 7 is a view similar to FIG. 6, and illustrating the pad means mounted upon the proximal end of the biopsy needle.

With attention now being directed to FIGS. 6 and 7 of the drawing, the knob generally designated 10 is shown adjacent biopsy needle structure 20, with structure 20 including an elongated hollow needle body 21, having a pair of radially extending finger gripping elements 22—22 extending therefrom, and with the needle further including a proximal end 23, which is an extension of hollow needle body 21. In order to gain access to the lumen of needle 21, the entire length of the needle is, of course, hollow.

Pad means 10 is shown mounted upon proximal end 23 of needle 20 in FIG. 7, with venting bore 16 being provided to transfer any entrapped air outwardly upon mounting of the pad 10 onto the needle 20.

In normal protocol, the surgeon advances needle 20 through the flesh of the patient until the sharpened distal tip 25 strikes the surface 26 of the bone to be sampled. Normally, a stylet will be employed which occupies the lumen of the needle, with the stylet being present while the needle 20 is being advanced through the flesh of the patient. In order to retain proper orientation of the stylet relative to the profile of the distal tip 25, a locking bore may be provided in the proximal end 23 of the needle, as illustrated in FIG. 6. In order to achieve penetration of the bone, needle 20 is rotated arcuately about its axis so as to permit any teeth, in the form of serrations, along the tip 25 to cut the bone surface. Force is applied, as required in order to achieve penetration. In FIG. 7, the distal tip 25 of needle 20 has passed sufficiently far through the surface of the bone so as to be in contact with the bone marrow tissue to be sampled. Distribution of forces applied during the penetration of bone 26 is achieved by palm engaging pad surface 12, as illustrated.

As indicated, the biopsy needle will contain a stylet which remains within the needle until the surface of the bone is reached. Upon removal of the stylet, the pad means 10 is slipped over the end of needle 20 so as to aid the elimination of any pain to the hand of the surgeon. Furthermore, risks of tearing of the surgical gloves worn by the surgeon are also reduced.

In certain other procedures, the surgeon will permit the stylet to remain within the needle until the marrow cavity is reached. At this point, the stylet is removed, the pad means inserted over the hub, and the biopsy sample is then started to be taken by lodging within the lumen.

While a variety of materials of construction may be employed for the pad means, it has been found that molded polytetrafluoroethylene is desirable from the standpoint of reduction of friction between the pad and the outer surface of the needle. Molded polytetrafluoroethylene is, of course, commercially available.

As has been indicated, the needle engaging sleeve is provided with a radially extending bore through the wall thereof to provide communication between the interior of the sleeve and atmosphere. Preferably, this bore is formed adjacent the juncture between the surface of the pad and the needle enveloping sleeve, in order to permit all of the entrapped air to be conveniently removed.

I claim:

1. In combination, a biopsy needle having an elongated hollow body member with a distal cutting edge and a proximal gripping portion, and a radially extending finger gripping means near the proximal end thereof; and pad means removably mounted upon said hollow body member at the proximal end thereof;

(a) said pad means comprising a generally disc-shaped element with first and second opposed major surfaces, said first surface being a palm engaging surface and with said second surface having a needle enveloping sleeve extending outwardly from the surface thereof; and (b) said needle enveloping sleeve having a radially extending bore formed through the wall thereof adjacent the juncture between said second pad surface and said sleeve for providing communication between the interior of said sleeve and atmosphere.

2. The combination as defined in claim 1 being particularly characterized in that said pad means is fabricated from polytetrafluoroethylene.

3. The combination as defined in claim 1 being particularly characterized in that said radially extending bore of said needle engaging sleeve is disposed along the juncture between said second pad surface and said sleeve.

* * * * *